United States Patent [19]

Ritleng

[11] Patent Number: 5,501,232
[45] Date of Patent: Mar. 26, 1996

[54] METHOD AND APPARATUS FOR PLACING TEAR DUCT DRAIN TUBES

[75] Inventor: Pierre Ritleng, Nice, France

[73] Assignee: F.C.I. (France Chirurgie Instrumentation), France

[21] Appl. No.: 236,270

[22] Filed: May 2, 1994

[30] Foreign Application Priority Data

May 4, 1993 [FR] France ..................... 93 05277

[51] Int. Cl.⁶ ..................... A61B 19/00
[52] U.S. Cl. ..................... 128/898; 606/108
[58] Field of Search ..................... 606/1, 108, 107; 623/4, 6; 604/8–10, 158, 160, 164, 264; 128/898

[56] References Cited

U.S. PATENT DOCUMENTS

| | | | |
|---|---|---|---|
| 4,305,395 | 12/1981 | Martinez | 604/28 |
| 4,660,546 | 4/1987 | Herrick et al. | 128/898 |
| 4,968,296 | 11/1990 | Ritch et al. | 606/108 |
| 5,178,604 | 1/1993 | Baerveldt et al. | 606/108 |

*Primary Examiner*—Stephen C. Pellegrino
*Assistant Examiner*—Glenn Dawson
*Attorney, Agent, or Firm*—Eckert Seamans Cherin & Mellott

[57] ABSTRACT

A method of putting a two-duct probe into place in the tear ducts using a hollow cylindrical cannula which is closed at its distal end, with an oblong opening being formed in the vicinity of the distal end. A slot extending proximally from the opening allows a narrowed portion of a guide filament attached to each end of a two-duct probe to pass in order to disengage the cannula from the filament. The cannula is removed from the tear duct and the ends of the guide filaments are each pulled into the nose to place the probe into the tear ducts.

9 Claims, 2 Drawing Sheets

METHOD AND APPARATUS FOR PLACING TEAR DUCT DRAIN TUBES

The present invention relates to a method of putting a two-duct ophthalmological intubation device into place, and to a cannula for performing the method.

BACKGROUND OF THE INVENTION

Two-duct drainage fixtures are constituted by a fine silicone tube designed to be intubed in the tear ducts in order to remedy certain dysfunctions such as stenoses that block said duct. The ducts communicate with the eye via meatuses located close to the nose in the top and bottom eyelids, and their function is to remove tear fluid via the nose.

It is known that in the event of these ducts being diseased, they can be intubed by means of a flexible filament or tube that unblocks the stenoses and reestablishes the flow of tear fluid. The problem solved by the invention is that of intubing tear ducts. At present, the silicone tube to be inserted in the ducts is terminated at each of its ends by a flexible metal mandrel that serves as a guide for following a twisting path. The drawback of that method of putting the tube into place is that it usually leads to bleeding, particularly when bringing the mandrels out into the nasal cavity, and in any event it is traumatic. Such a method is described in U.S. Pat. No. 4,380,239-Crawford et at.

The problem can be remedied using the Busse technique in association with a Jünemann probe. The Busse technique essentially consists in passing a fine filament along the ducts and then in using the filament to pull the silicone tube which is of greater diameter.

A Jünemann probe is in the form of a hollow cannula having fins for grasping purposes at its top end and a lateral hole at its bottom end, its leading tip being closed. The leading end of the probe is initially cathetered in the meatus in a position that is slightly inclined relative to the horizontal so as to penetrate into the horizontal portion of the duct, after which it is caused to rotate through substantially 90° and a fine guide filament, e.g. of prolene, is pushed inside the probe and then inside the nasal cavity from which it can be retrieved by means of a hook or tweezers. The Jünemann probe is then slid from the other end of the filament from which it escapes. This operation is repeated in each of the two ducts. After which each of the guide filaments is united to the end of the probe proper.

That technique has the advantage of avoiding bleeding and of being non-traumatic. However, compared with the two-duct probes mentioned above it requires more time and it is considerably more complex. The length of time required is due in particular to the fact that the surgeon must make the connection between the prolene filament and the silicone tube after extracting the probe.

The surgeon therefore needs to perform the following operations in succession:

a) inserting the cannula in a tear duct;

b) pushing the guide filament into the cannula;

c) pulling the guide filament from inside the nasal cavity;

d) extracting the cannula from the tear duct and from the filament by making it slide upwards along the guide filament;

e) connecting the guide filament to the silicone tube;

f) causing the assembly comprising the guide filament and the silicone tube to move along the tear duct by pulling from below and pushing from above in small successive movements in order to avoid disconnecting the filament from the tube; and g) once the silicone tube appears in the nasal cavity, separating the filament from the tube and pulling thereon.

After which the same operation needs to be performed in the other meatus.

The operation which is the most lengthy and the most difficult is step f). It is not possible for the surgeon to fix the guide filament to the silicone tube in advance since the cannula must be removed from the guide filament before the connection can be made.

OBJECTS AND SUMMARY OF THE INVENTION

An object of the present invention is to mitigate that drawback and to make available to the surgeon a guide filament and silicone tube assembly from which the probe can easily be removed, thereby avoiding or facilitating steps e), f), and g).

According to the present invention, the method of putting a two-duct probe constituted by a silicone tube into place by means of an intubing cannula constituted by a hollow cylindrical body closed at its bottom end whose outside diameter is less than the outside diameter of the silicone tube that presents a lateral opening close to its leading end consists in:

providing each of the ends of the silicone tube with a guide filament of diameter smaller than the inside diameter of the hollow cylindrical body;

providing a longitudinal slot inside the hollow cylindrical body and extending from the opening to the back end of the body;

forming a narrow zone in the guide filament, the diameter of the narrow zone being slightly less than the width of the slot;

inserting the cannula in a meatus;

sliding the guide filament along the duct until it becomes apparent inside the nose; and causing the cannula to pass over the narrowed portion so as to disengage the guide filament.

It therefore suffices to cause the cannula to slide over the filament until the narrower zone comes level with the slot, and then to disengage the cannula by causing it to pivot relative to the filament.

Because of the invention, the connection between the guide filament of prolene and the silicone tube can be made in the factory, e.g. by means of adhesive (step f) and the surgeon can pull on the guide filament that appears in the nose substantially continuously, thereby achieving a considerable saving in time (step g).

BRIEF DESCRIPTION OF THE DRAWING

Other characteristics and advantages of the invention appear from the following description of a particular embodiment, given solely by way of non-limiting example and making reference to the accompanying drawing, in which.

MORE DETAILED DESCRIPTION

Figure 1:
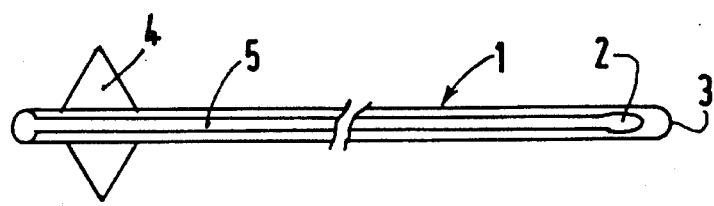
FIG. 1 is a plan view of a probe of the invention.

In FIG. 1, it can be see that the cannula comprises a cylindrical hollow body 1 whose front or bottom end 3 is closed. In the vicinity of this end there is an oblong hole or opening 2. At the other end of the cannula there are fins 4 for grasping purposes.

According to the invention, a longitudinal slot 5 extends from the opening 2 along the entire length of the cannula. This slot may be made by electroerosion, for example.

Given anatomical type constraints, the cannula is 0.5 mm in diameter and the slot is 0.25 mm wide. The length of the cannula is 100 mm, but that dimension is not critical.

Figure 2:
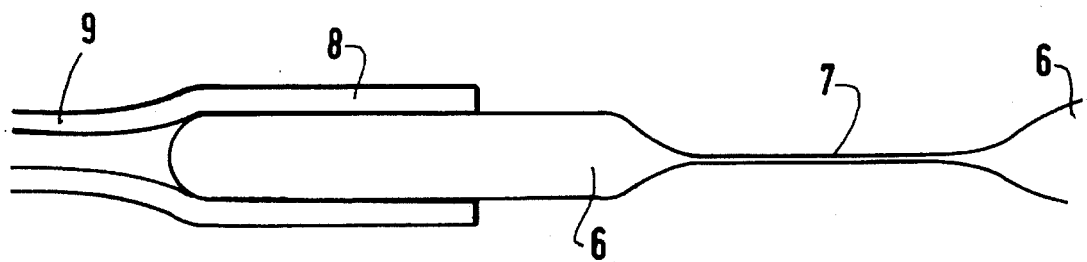
FIG. 2 is a view showing the connection between the silicone tube and the prolene filament.

A prolene filament 6 (FIG. 2) is inserted in said cannula, the diameter of the filament being 0.4 mm so as to enable it to slide freely inside the cannula. As can be seen in FIG. 2, the prolene filament is connected to the front end 8 of a silicone tube 2 in which it is a force-fit and optionally retained by adhesive. The inside diameter of the tube 9 is 0.3 mm, and after the filament 6 has been inserted therein its outside diameter is 0.64 mm, for example.

Figure 3:
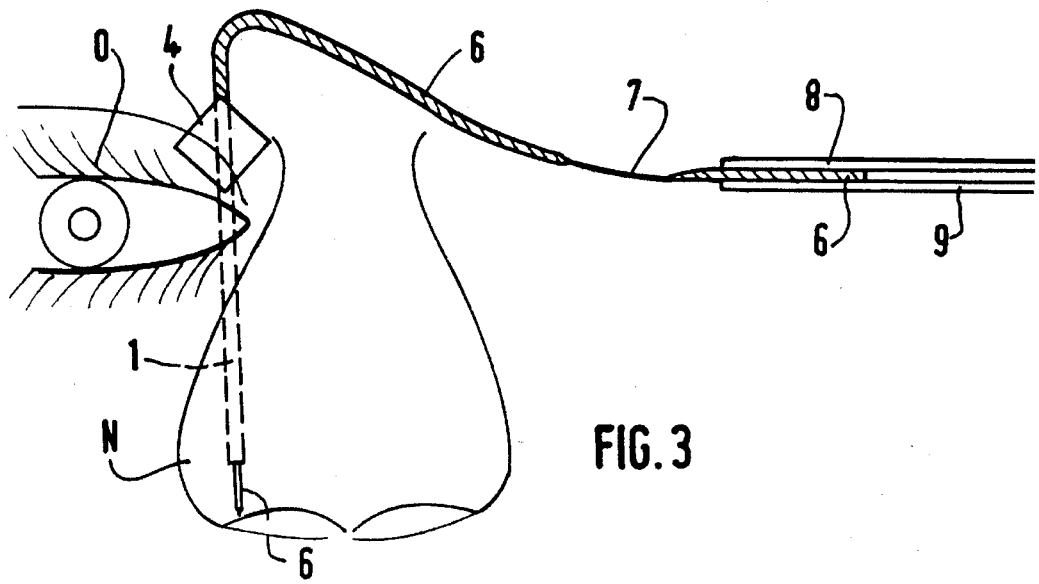
FIG. 3 is a view of the probe inside a tear duct.
Figure 4:
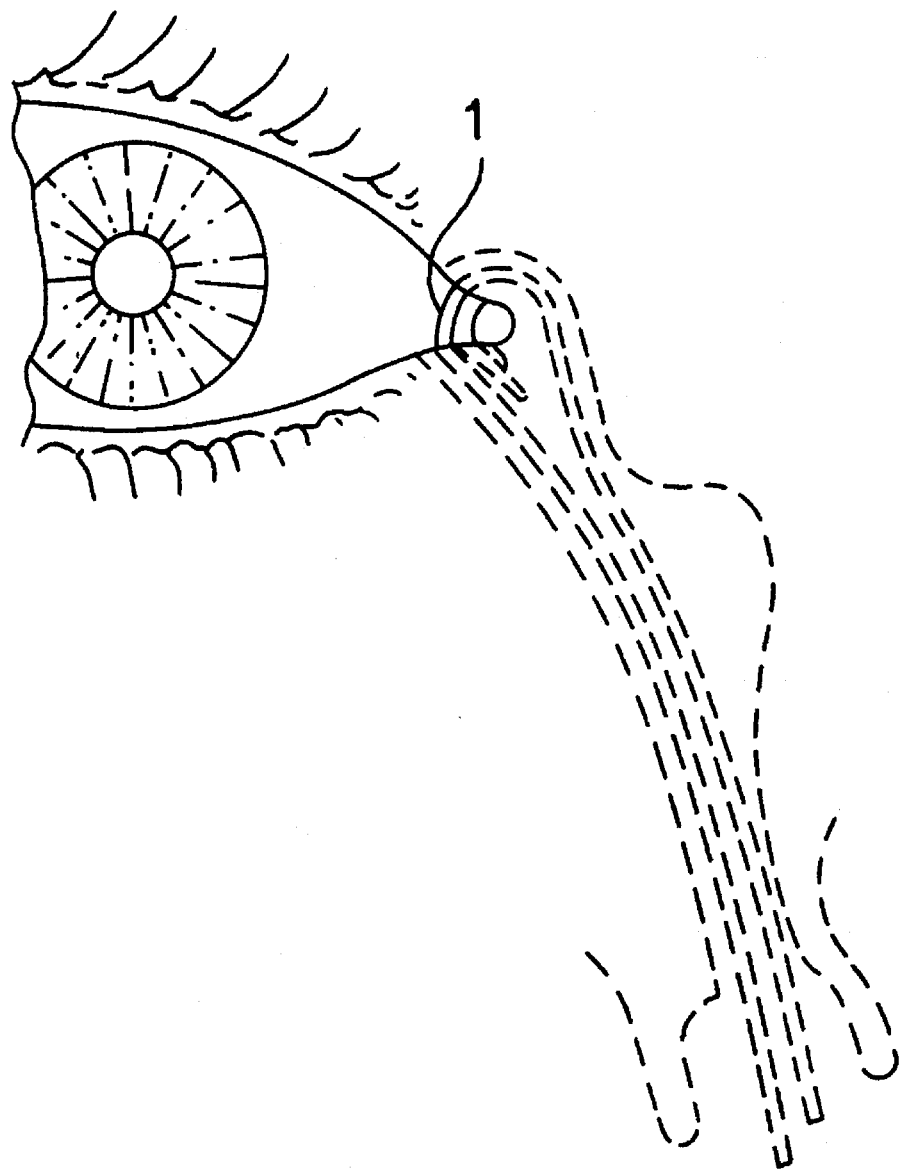
FIG. 4 is an elevation view schematically illustrating the finished placement of the tube.

The above-mentioned elements can be seen in FIG. 3. The cannula 1 is inserted into the bottom tear duct of an eye O and it penetrates into the nasal cavity N. During such insertion, the cannula 1 contains the filament 6 extending up to its opening 2. After insertion, the filament 6 is pushed by means of tweezers (not shown) until its bottom end appears inside the nose. Then while holding the filament, the cannula 1 is disengaged from the tear duct and caused to slide along the filament 6 until it reaches the narrowed zone 7 thereof. Then it is disengaged from the filament 6 by a pivoting movement and the filament is pulled down, thereby entraining the tube 9 which in turn penetrates bit by bit into the corresponding tear duct.

The same operation is repeated with the second tear duct and the operation is completed by ligating the two tube ends 9 inside the nose.

I claim:

1. A method of inserting a two-duct intubation device into place, the intubation device having a silicone tube with two opposite ends for coupling between a patient's tear ducts and nose, using an intubing cannula with a front end and a rear end, the cannula comprising a hollow cylindrical body closed at the from end, the cannula having an outside diameter that is less than an outside diameter of the silicone tube and having a lateral opening adjacent the front end of the cylindrical body and a longitudinal slot extending from the lateral opening to the rear end of the cannula, the method comprising the steps of:

providing each end of the silicone tube with a guide thread having a diameter that is smaller than an inside diameter of the hollow cylindrical body and smaller than a width of the lateral opening in the hollow cylindrical body, such that each guide thread can be advanced through the cylindrical body and the lateral opening;

providing a narrowed length along at least a zone of each guide thread, at which each guide thread can be passed laterally through the longitudinal slot;

inserting the cannula in a meatus and positioning a first one of the guide threads in the cannula up to the lateral opening;

causing the first guide thread to advance through the cannula and through the lateral opening, along the tear duct until the first guide thread becomes apparent inside the nose; and disengaging the cannula from the meatus and from the guide thread by passing the first guide thread laterally through the longitudinal slot and pulling the tube into the tear duct via the first guide thread.

2. The method of claim 1, further comprising inserting the cannula in another meatus, positioning a second guide thread attached to the other of the opposite ends of the tube in the cannula up to the lateral opening, causing the second guide thread to advance through the cannula and through the lateral opening along the tear duct until the second guide thread becomes apparent inside the nose, and disengaging the cannula from the meatus and removing the cannula from the second guide thread by passing the second guide thread laterally through the longitudinal slot.

3. The method of claim 2, further comprising drawing both opposite ends of the silicone tube into the nose via said guide threads and ligating opposite ends of the tube inside the nose.

4. The method of claim 1, wherein said zone of each guide thread is of limited length, substantially corresponding to a length along the cannula from the lateral opening to the rear end, and further comprising positioning the cannula at the narrowed zone before removing the cannula from the first guide thread.

5. An intubing cannula for inserting an intubation device having a duct coupled to a guide thread into place, comprising:

a hollow cylindrical body open at a rear end and closed at a leading end and having a lateral opening adjacent to the leading end through which the guide thread can be advanced, the hollow cylindrical body including a longitudinal slot extending from the lateral opening to the rear end, whereby the guide thread and the hollow cylindrical body are laterally disengageable by passing the guide thread through the longitudinal slot.

6. The cannula of claim 5, wherein the cannula is dimensioned for insertion in a tear duct, the cannula having a diameter of about 0.5 mm and the longitudinal slot has a width of about 0.25 mm.

7. The cannula of claim 5, further comprising grasping means attached to the of the cannula.

8. In combination, a two-duct ophthalmological device and an intubing cannula, said ophthalmological device comprising:

a silicone tube having guide filaments fixed to each of its opposite ends for guiding the opposite ends through tear ducts and of a patient's eye such that the opposite ends form two ducts;

said intubing cannula being configured for placing the guide filaments in the tear ducts, the intubing cannula having a hollow cylindrical body open at a rear end and closed at a leading end and comprising a lateral opening adjacent to the leading end through which one of the guide filaments can be advanced, the hollow cylindrical body including a longitudinal slot extending from the lateral opening to the rear and, whereby the hollow cylindrical body is laterally removable from the guide filaments through the longitudinal slot.

9. The combination of claim 8, wherein the guide filament has a zone of reduced thickness along a length of the guide filament substantially equal to a length of the longitudinal slot of the cannula from the lateral opening to the rear end.

* * * * *

UNITED STATES PATENT AND TRADEMARK OFFICE
CERTIFICATE OF CORRECTION

PATENT NO. : 5,501,232
DATED : March 26, 1996
INVENTOR(S) : Pierre Ritleng

It is certified that error appears in the above-indentified patent and that said Letters Patent is hereby corrected as shown below:

Column 3, Claim 1, line 44, delete "from" and substitute therefor —front—.

Column 4, Claim 7, line 43, after the first instance of "the", insert —cylindrical body adjacent the rear end—.

Column 4, Claim 8, line 50, after the word "ducts;" insert —and—.

Column 4, Claim 8, line 53, delete "having" and insert therefor —comprising—.

Column 4, Claim 8, line 58, delete "and" and substitute therefor —end—.

Column 4, Claim 9, lines 61-62, delete "filament has" and substitute therefor —filaments have—.

Column 4, Claim 9, line 63, change "filament" to —filaments—.

Column 4, Claim 8, line 54, delete "comprising" and insert therefor —having—.

Signed and Sealed this

Twenty-second Day of April, 1997

Attest:

BRUCE LEHMAN

*Attesting Officer*

*Commissioner of Patents and Trademarks*